(12) United States Patent
Thoms et al.

(10) Patent No.: US 8,342,822 B2
(45) Date of Patent: Jan. 1, 2013

(54) SUCTION DEVICE FOR DENTAL, MEDICAL AND INDUSTRIAL PURPOSES

(75) Inventors: Michael Thoms, Bietigheim-Bissingen (DE); Juergen Schnepf, Heilbronn (DE); Andreas Haegele, Weinstadt (DE)

(73) Assignee: Duerr Dental AG (DE)

( * ) Notice: Subject to any disclaimer, the term of this patent is extended or adjusted under 35 U.S.C. 154(b) by 522 days.

(21) Appl. No.: 12/518,536

(22) PCT Filed: Dec. 11, 2007

(86) PCT No.: PCT/EP2007/010806
§ 371 (c)(1),
(2), (4) Date: Jul. 21, 2009

(87) PCT Pub. No.: WO2008/071388
PCT Pub. Date: Jun. 19, 2008

(65) Prior Publication Data
US 2010/0034673 A1 Feb. 11, 2010

(30) Foreign Application Priority Data
Dec. 12, 2006 (DE) .......................... 10 2006 058 955

(51) Int. Cl.
*F04B 35/04* (2006.01)
(52) U.S. Cl. .................................................. 417/423.7
(58) Field of Classification Search .................. 417/313, 417/423.1, 423.7, 424.1; 494/84, 42, 50, 494/51, 52; 433/92, 104, 115, 130, 131, 433/132; 210/360.1, 380.1, 143, 188, 512.1
See application file for complete search history.

(56) References Cited

U.S. PATENT DOCUMENTS

| | | | | |
|---|---|---|---|---|
| 3,490,209 A | * | 1/1970 | De Groote et al. | 55/430 |
| 4,554,473 A | * | 11/1985 | Muller | 310/67 R |
| 4,564,374 A | * | 1/1986 | Hofmann | 95/24 |
| 4,684,345 A | * | 8/1987 | Cattani | 433/92 |

(Continued)

FOREIGN PATENT DOCUMENTS

DE 100 10 077 A1 9/2001

(Continued)

OTHER PUBLICATIONS

Yedamale, P. "Brushless DC (BLDC) Motor Fundamentals" 2003, Microchip Technology Inc.*

(Continued)

*Primary Examiner* — Devon Kramer
*Assistant Examiner* — Christopher Maxey
(74) *Attorney, Agent, or Firm* — Factor Intellectual Property Law Group, Ltd.

(57) ABSTRACT

A suction device for dental, medical and industrial purposes with a radial fan with a suction side and a delivery side. An air outlet of a centrifugal separator is connected to the suction side of the fan. At least one drive motor controlled by a control unit, and in the form of a rotating electric motor, drives the fan and the separator. A fan drive motor and a separator drive motor are arranged, uncoupled in terms of rotation, one behind the other on a common shaft fixed to the housing. The respective stators are supported by the common shaft. The rotating parts of the fan are connected to the rotor of the fan drive motor, and the rotating parts of the separator are connected to the rotor of the separator drive motor and are mounted to rotate coaxially with respect to the shaft fixed to the housing.

21 Claims, 7 Drawing Sheets

U.S. PATENT DOCUMENTS

| | | | |
|---|---|---|---|
| 4,824,333 A | 4/1989 | Erickson, Jr. | |
| 4,842,478 A * | 6/1989 | Durr et al. | 415/169.2 |
| 4,891,041 A * | 1/1990 | Hohmann et al. | 494/62 |
| 5,018,971 A * | 5/1991 | Trawoger et al. | 433/92 |
| 5,311,640 A * | 5/1994 | Holland | 15/353 |
| 5,330,641 A * | 7/1994 | Cattani | 210/188 |
| 5,407,565 A * | 4/1995 | Austin et al. | 210/188 |
| 5,484,282 A * | 1/1996 | Trawoger et al. | 433/92 |
| 5,610,458 A * | 3/1997 | Baker et al. | 310/68 R |
| 5,618,410 A * | 4/1997 | Wallace et al. | 210/123 |
| 5,693,125 A * | 12/1997 | Dean | 96/157 |
| 5,693,221 A | 12/1997 | Ellinghaus | |
| 6,205,405 B1 * | 3/2001 | Pouvreau | 702/41 |
| 6,372,006 B1 * | 4/2002 | Pregenzer et al. | 55/406 |
| 6,570,353 B2 * | 5/2003 | Krotsch et al. | 318/400.24 |
| 6,956,342 B1 * | 10/2005 | Fang | 318/400.08 |
| 7,250,733 B2 * | 7/2007 | De Filippis et al. | 318/400.01 |
| 7,420,307 B2 * | 9/2008 | Lelkes et al. | 310/180 |
| 7,732,957 B2 * | 6/2010 | Nomura et al. | 310/67 R |
| 7,767,168 B2 * | 8/2010 | Namespetra et al. | 422/186.12 |
| 8,030,809 B2 * | 10/2011 | Horng et al. | 310/43 |
| 2001/0012814 A1 * | 8/2001 | May et al. | 494/24 |
| 2002/0185984 A1 * | 12/2002 | Gold et al. | 318/17 |
| 2004/0031391 A1 * | 2/2004 | Grimm et al. | 96/209 |
| 2004/0061470 A1 * | 4/2004 | Ito et al. | 318/565 |
| 2004/0251860 A1 * | 12/2004 | Ehsani et al. | 318/254 |
| 2006/0120903 A1 * | 6/2006 | Iwasaki et al. | 417/423.1 |
| 2007/0031131 A1 * | 2/2007 | Griffitts | 388/811 |
| 2007/0065300 A1 * | 3/2007 | Mariani et al. | 417/243 |
| 2009/0298011 A1 * | 12/2009 | Thoms et al. | 433/92 |
| 2010/0204032 A1 * | 8/2010 | Pregenzer et al. | 494/14 |
| 2011/0143311 A1 * | 6/2011 | Thomas et al. | 433/92 |

FOREIGN PATENT DOCUMENTS

| | | |
|---|---|---|
| DE | 10 2004 028 942 A1 | 1/2006 |
| EP | 0 680 289 B1 | 8/1998 |
| EP | 1 366 728 A1 | 12/2003 |
| WO | 2007/112814 A1 | 10/2007 |

OTHER PUBLICATIONS

Lelkes, A., Krotsch, J., De Doncker, R.W. "Low-Noise External Rotor BLDC Motor for Fan Application" 2002 IEEE.*

* cited by examiner

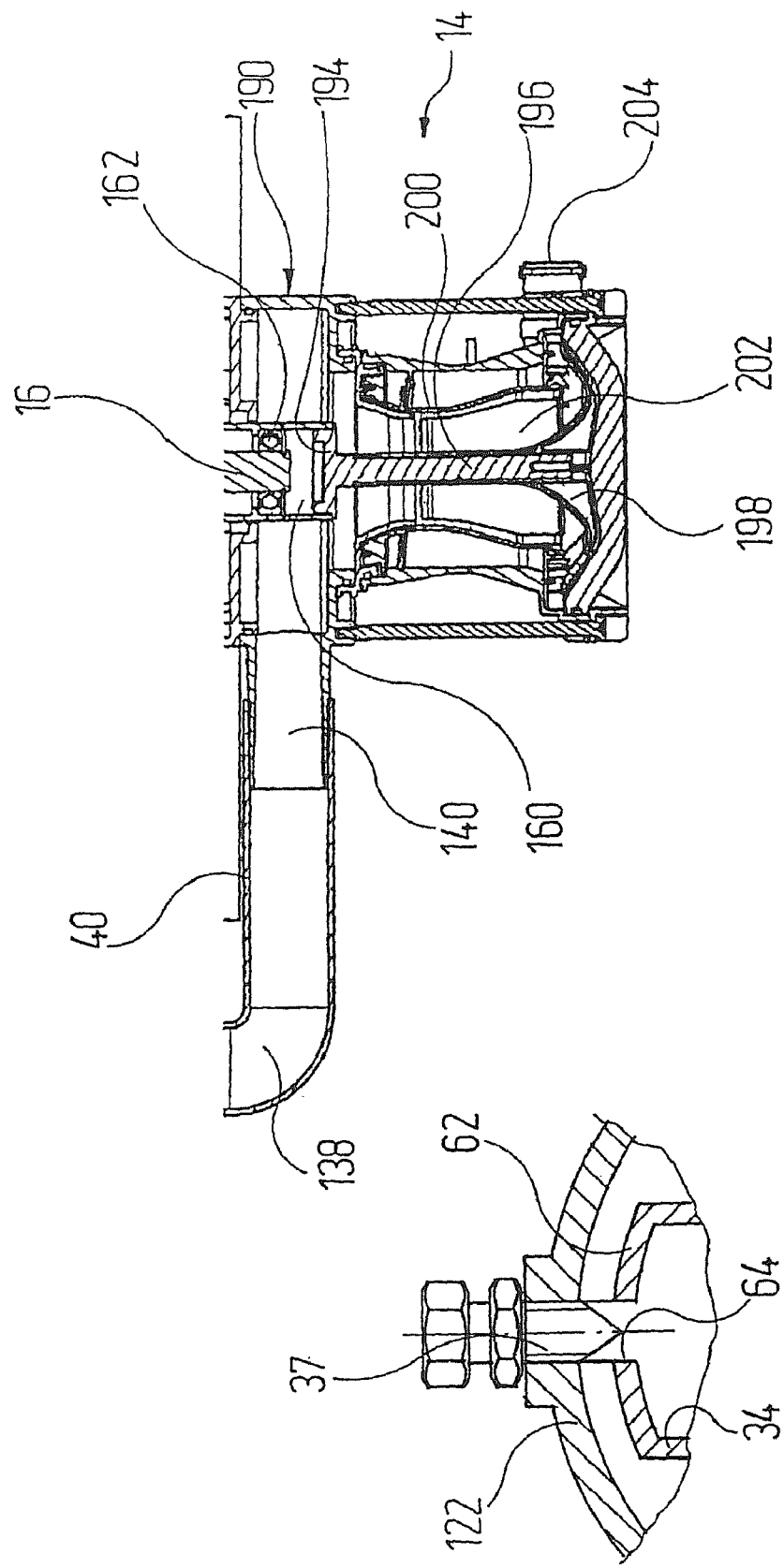

SUCTION DEVICE FOR DENTAL, MEDICAL AND INDUSTRIAL PURPOSES

RELATED APPLICATIONS

This application claims the filing benefit of International Patent Application No. PCT/EP2007/010806, filed Dec. 11, 2007, which claims the filing benefit of German Patent Application No. 10 2006 058 955.6 filed Dec. 12, 2006, the contents of which are incorporated herein by reference.

TECHNICAL FIELD

The present invention relates to a suction device for dental, medical and industrial purposes, and more specifically, to a suction device for dental, medical and industrial purposes with, a radial fan which exhibits a suction side and a pressure side; a centrifugal separator, the air outlet of which is connected to the suction side of the radial fan; at least one drive unit which includes an electric motor and for driving the radial fan and the centrifugal separator; and a control unit for the drive unit.

BACKGROUND OF THE INVENTION

Suction devices of such a type are known in the form of commercial products. In the dental field they serve for applying underpressure to a saliva siphon and/or to a suction cannula via which water, mucus, blood and drill cuttings—including, in particular, hard dental tissue and amalgam particles—are aspirated out of the mouth of a patient.

From DE 100 10 077 A1 a suction device of such a type is known wherein the rotating parts of the radial fan and of the centrifugal separator are seated on a common shaft arrangement which is driven by a drive motor. In this manner, the fan wheels of the radial fan and a guide wall of a centrifugal drum of the centrifugal separator are always driven at the same rotational speed.

The present invention is directed to resolving these and other matters.

SUMMARY OF THE INVENTION

By means of the present invention, a suction device for dental, medical and industrial purposes with, a radial fan which exhibits a suction side and a pressure side; a centrifugal separator, the air outlet of which is connected to the suction side of the radial fan; at least one drive unit which includes an electric motor and for driving the radial fan and the centrifugal separator; and a control unit for the drive unit is to be developed in such a way that the rotating parts of the radial fan and the rotating parts of the centrifugal separator can be rotated at different rotational speeds and the suction device is nevertheless compact overall and has a high efficiency of separation and of generation of underpressure.

The suction device according to the invention has the advantage that the radial fan and the centrifugal separator are driven independently of one another. The centrifugal separator can consequently run, as a rule, at distinctly lower rotational speeds than the fan. By virtue of the series arrangement of the drive motors, the suction device is of very compact structure overall. The specified design of the drive unit makes do without a transmission, as a result of which the suction device according to the invention can be produced easily and inexpensively and has a particularly compact structure.

With the radial fan of the suction device according to the invention, the pressure/volume characteristic is distinctly flatter in comparison with side-channel machines known from the state of the art. With the suction device according to the invention with the radial fan, the power demand is proportional to the quantity of air and not proportional to the pressure, as is the case with the known side-channel machines. In this manner, the waste heat is less at all operating points than in conventional dental suction machines.

Both the radial fan and the centrifugal separator are controllable and adjustable in rotational speed via the control unit. In this connection, the respective rotational speed may be preset to be constant. This is preferred when—in the course of a dental treatment, for example—the suction power of the suction device is to be varied, in order by this means to obtain advantages in the course of the treatment.

Furthermore, in this manner several workstations can also be operated parallel to one another.

Alternatively, the rotational speed can also be regulated in pressure-led manner. This has the advantage that a constant suction underpressure can be obtained even when several workstations are attached to the suction device in parallel, which may result in greatly fluctuating suction-air requirements. Stabilisation of the suction underpressure is often necessary, in particular, in the course of the dental treatment.

The use of the radial fan has the advantage furthermore that said fan permits axially and radially larger spacings from stationary housing parts than is possible in conventional suction machines known from the state of the art. This facilitates assembly. The radial fan is therefore also distinctly less susceptible to deposits in the flow space in comparison with known side-channel vacuum machines.

By virtue of the fact that the centrifugal separator can be operated at lower rotational speeds than the radial fan, the drive mechanism in the water-conducting regions of the centrifugal separator can be operated with distinctly lower losses of energy than is the case at the higher rotational speeds of the radial fan.

Advantageous further developments of the invention are specified in the dependent claims.

An axle, fixed with respect to the housing, on which two rotors of the two drive motors are supported—e.g. fan drive motor and the separator drive motor are arranged on a common axle which is fixed with respect to the housing, the respective stators being connected to the axle, the rotating parts of the radial fan being connected in non-rotating manner to the rotor of the fan drive motor and the rotating parts of the centrifugal separator being connected in non-rotating manner to the rotor of the separator drive motor and being supported in rotating manner coaxially relative to the axle which is fixed with respect to the housing. The axle may serve as carrying part, so that these surrounding housing parts can be manufactured from lightweight material, plastic for example. A common bearing axle also has the advantage of a particularly compact and robust overall structure which can be assembled with little effort.

The arrangement of rotor bells in each instance at the ends of the axle which is fixed with respect to the housing and carry the magnet segments on their insides is particularly space-saving.

Electronically commutated drive motors, e.g., fan drive motor and separator drive motor, are electronically commutated and can be operated at high rotational speeds and have a good efficiency at low power consumption. Electronically commutated drive motors may furthermore be operated, within certain limits, with variable input mains voltages, something which is not possible with asynchronous motors known from the state of the art. They can be employed at different mains frequencies and mains voltages, without different designs of the rotor being necessary. In this manner, the manufacturing effort and the delivery effort are distinctly reduced.

The use of magnetic-field transducers on commutator plates mounted on the axle which is fixed with respect to the housing enables the realisation of wear-free commutators.

A suction device wherein a radial fan is in two stages, preferentially two impellers which revolve in assigned working spaces (housings) which are connected to one another via at least one deflecting stage being connected in series coaxially to the rotor of the fan drive motor has turned out to be particularly advantageous with regard to the pressure that is capable of being generated with the suction device. Greater pressures can be generated with a two-stage radial fan than with single-stage fans. On the other hand, in comparison with three-stage or multi-stage radial fans a two-stage radial fan has the advantage that the pressure losses by reason of deflections of air within the housing of the radial fan are smaller.

With a ventilator wheel for cooling thermally loaded structural components—in particular, the control unit, the stators, and/or bearings of the rotors—preferentially situated between the fan drive motor and the separator drive motor coaxially relative to the axle which is fixed with respect to the housing, and is arranged in rotating manner and is connected in driving relationship to one of the drive motors, in particular to the separator drive motor, such that the thermally loaded structural components inside the suction device can be cooled effectively. In this manner, continuous operation of the suction device can be realised, which is necessary especially in the dentistry field, particularly in a dental practice or in a dental hospital. The service life of the thermally loaded structural components is thereby increased, and the suction device can also be used permanently at high rotational speeds of the fan in the aforementioned fields of application. The arrangement of the ventilator wheel between the two drive motors in coaxial manner is space-saving; in addition, drive by one of the two drive motors has the advantage that no separate ventilator-wheel motor is necessary.

A cavity extending in the longitudinal direction, which is provided with uninterrupted inlet connections and output connections for cooling air to the generated surface and to a front side of the axle, respectively, in the axle which is fixed with respect to the housing in the region of bearings enables cooling air to be conducted through, and consequently enables an internal cooling of the axle and of the associated bearings. In this manner, an overheating of the bearings at high rotational speeds is prevented, and in this way their service life is increased.

In accordance with a further aspect of the invention, a control unit can be integrated within the suction device in a particularly space-saving manner such that the control unit is arranged in a region between the fan drive motor and the separator drive motor. In comparison with suction devices that are known on the market, this has the advantage that no external control boxes with protective devices and overcurrent tripping devices are required, so that the assembly effort and the costs are distinctly lower. With a control unit for electronically commutated drive motors, furthermore a current limitation can be realised more easily than with an overcurrent protection that is employed in three-phase motors known from the state of the art, particularly since in the case of three-phase motors an overcurrent protection has to be provided for each of the three phases.

These and other objects and advantages will be made apparent from the following brief description of the drawings and the detailed description of the invention

BRIEF DESCRIPTION OF THE DRAWINGS

FIG. 7 is an axial section through the centrifugal separator of the suction fan according to FIG. 1; and, FIG. 8 is axial section through an adjustable throttle for the suction unit of FIGS. 1 and 5.

DETAILED DESCRIPTION OF THE PRESENT INVENTION

Figure 1:
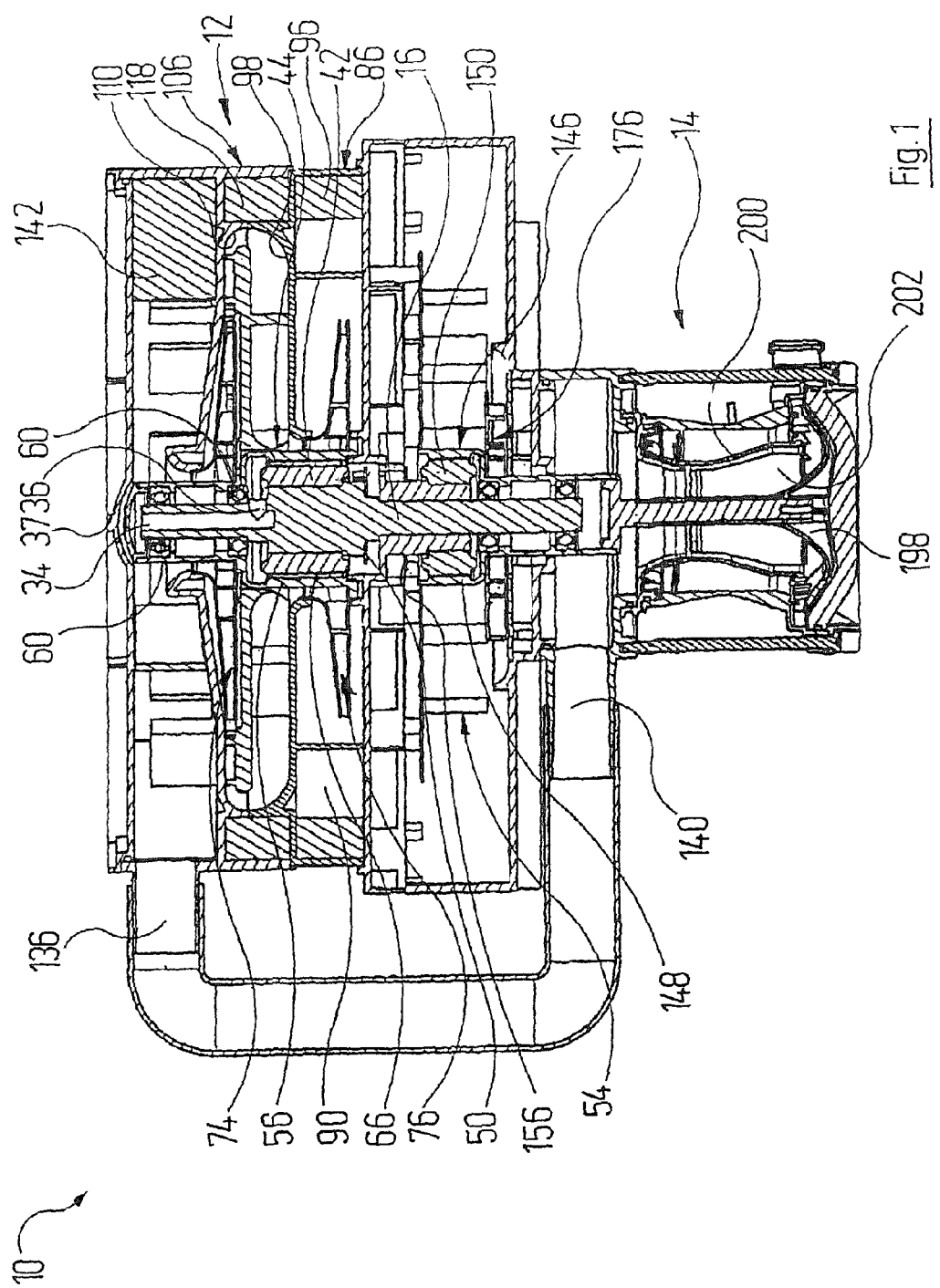
FIG. 1 schematically depicts an axial section through a dental suction fan with an integrated radial fan and with a centrifugal separator for aspirated liquid and solid constituents, wherein for the sake of clarity only the reference symbols for the most important components have been recorded.
Figure 2:
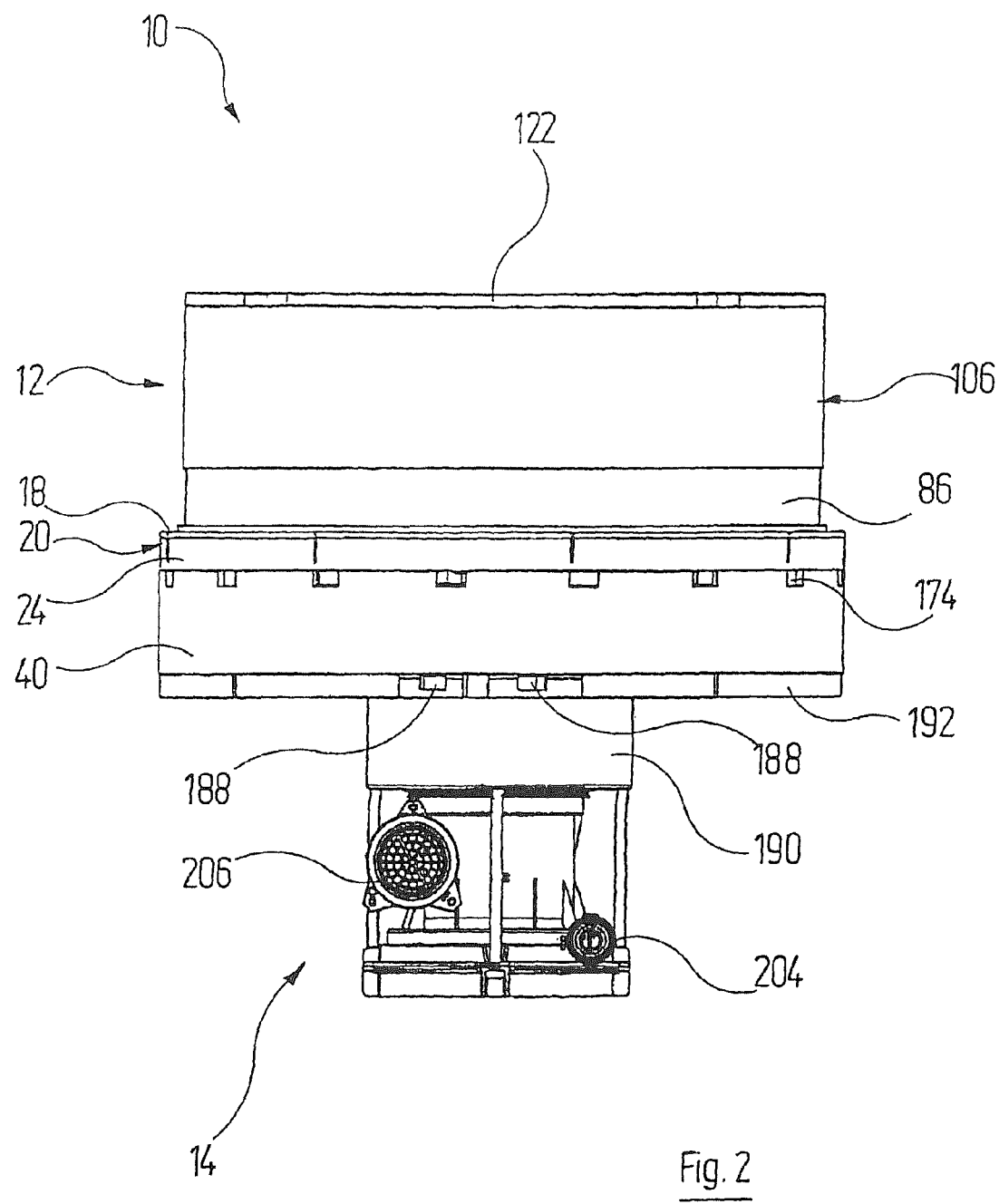
FIG. 2 schematically depicts a side view of the dental suction fan from FIG. 1.
Figure 3:
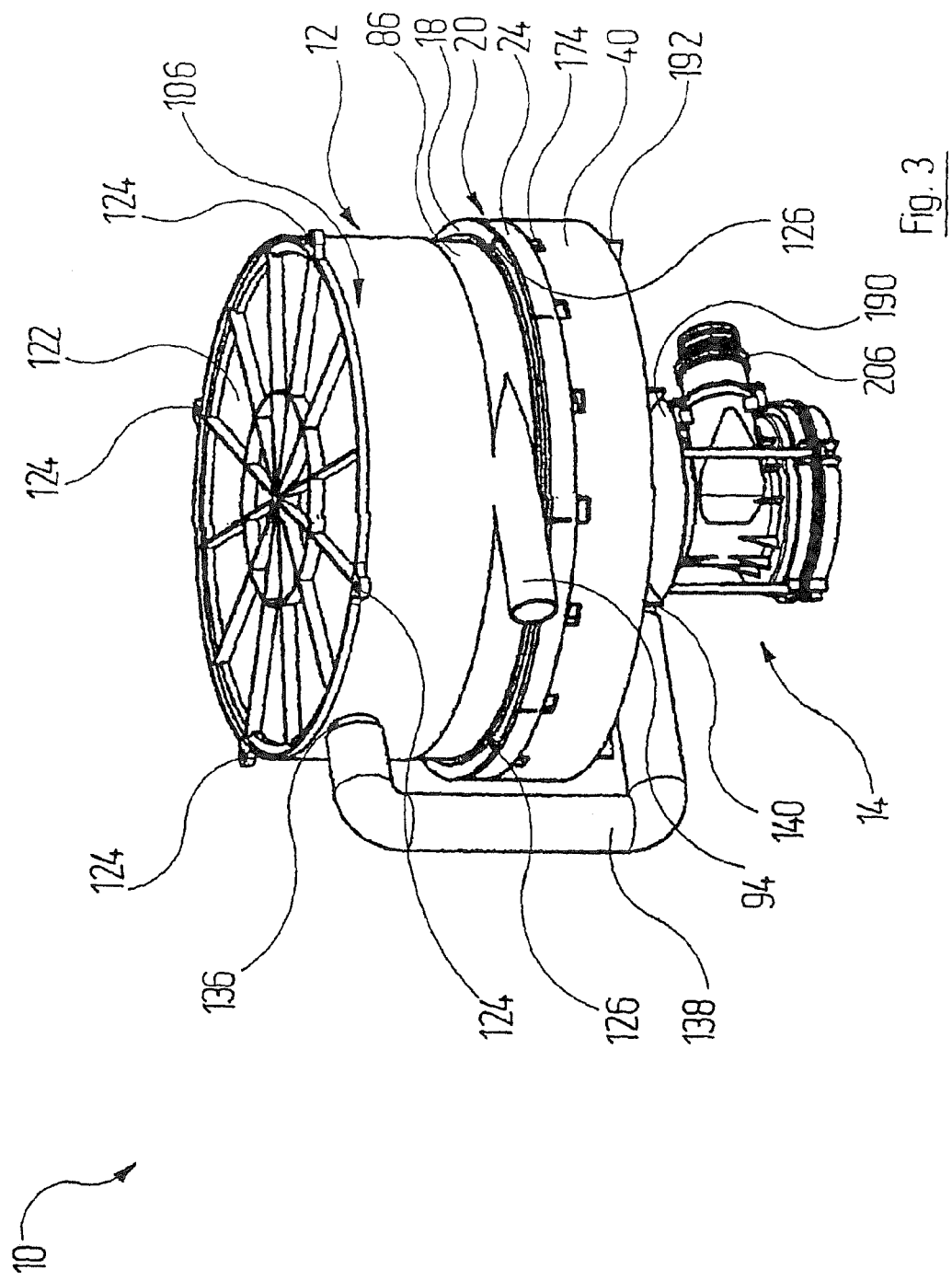
FIG. 3 schematically depicts an isometric representation of the dental suction fan from FIGS. 1 and 2.
Figure 4:
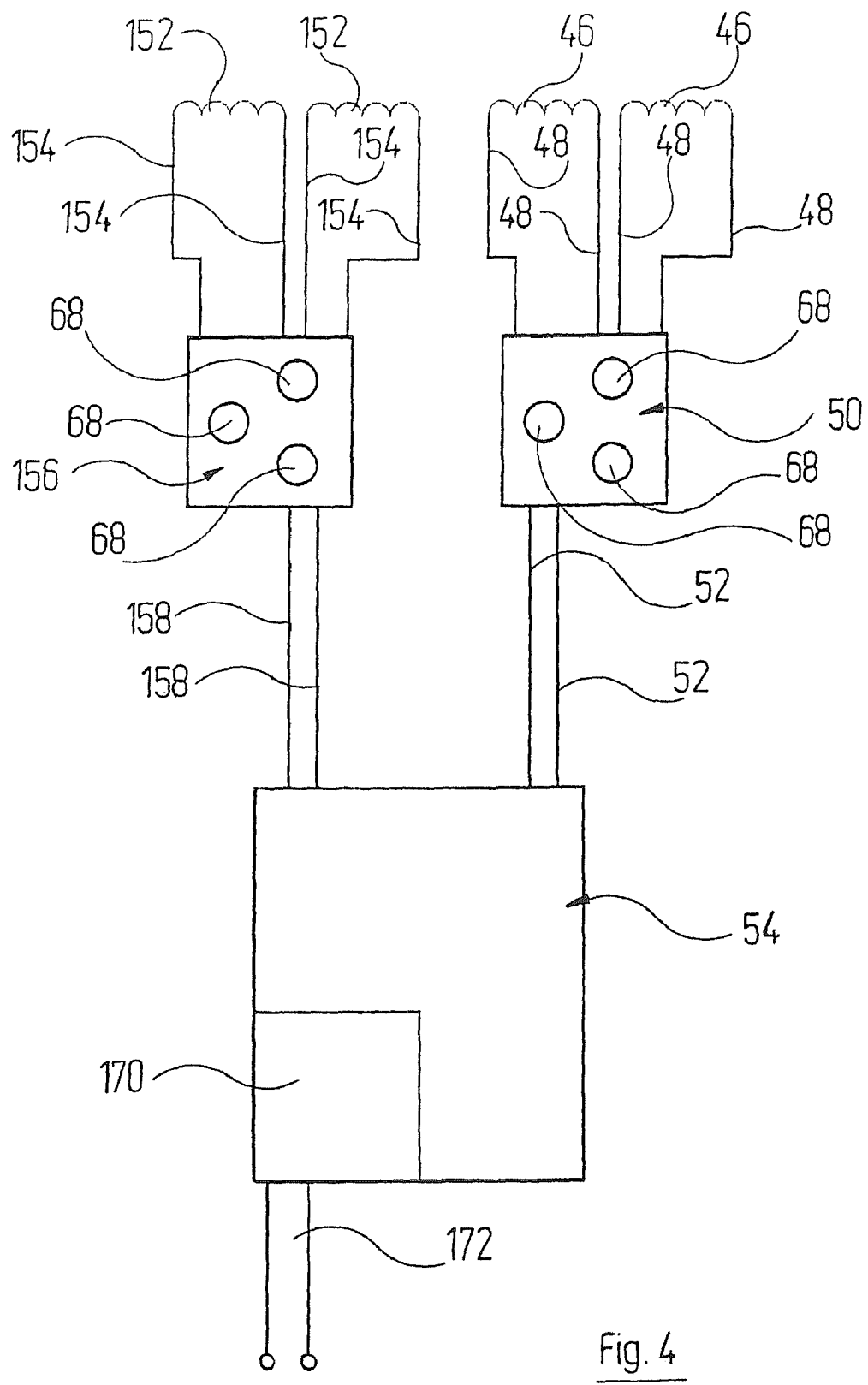
FIG. 4 is a schematic block diagram of the dental suction fan from FIGS. 1 to 3.
Figure 5:
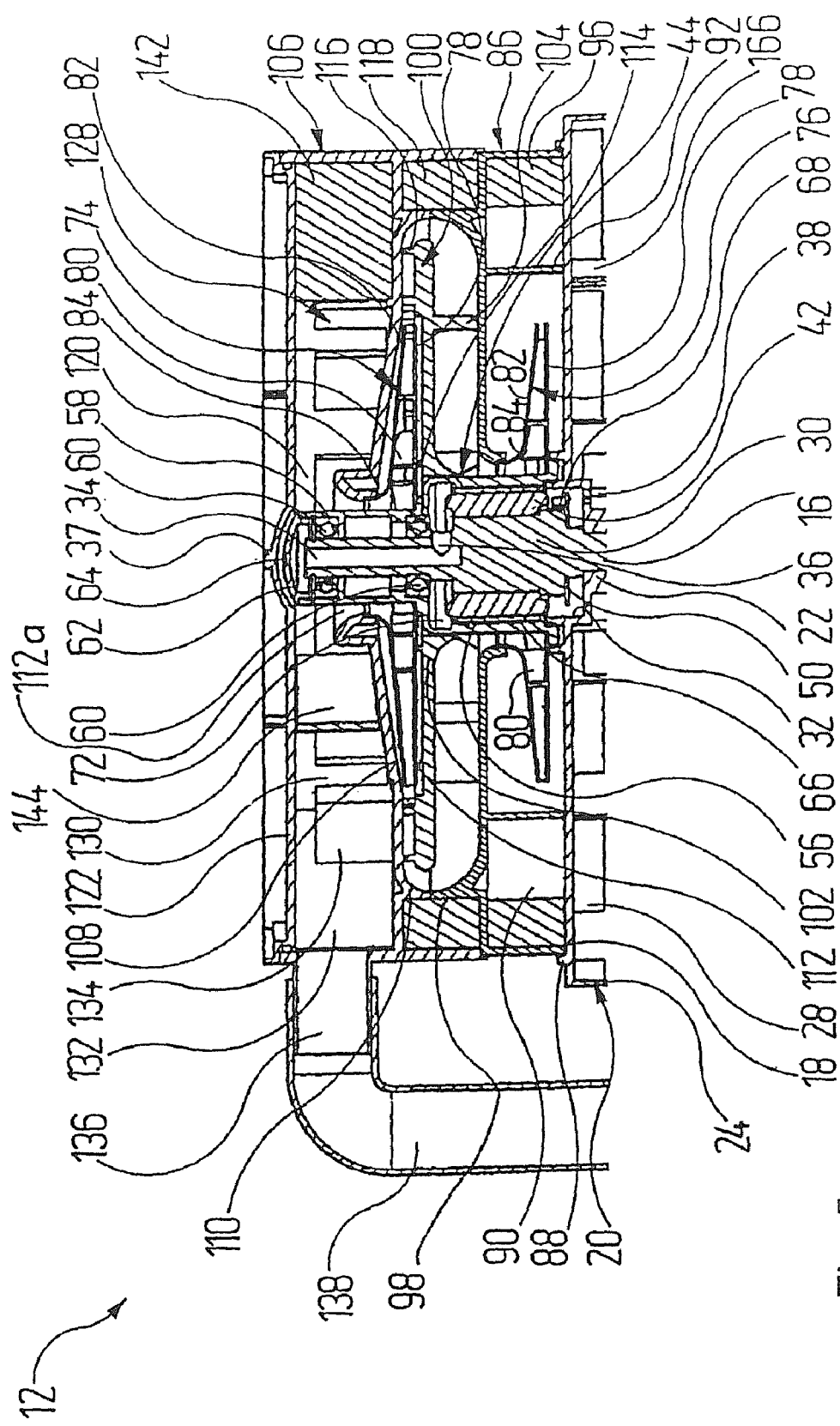
FIG. 5 is an axial section through a radial fan of the suction fan of FIG. 1 and its drive motor.
Figure 6:
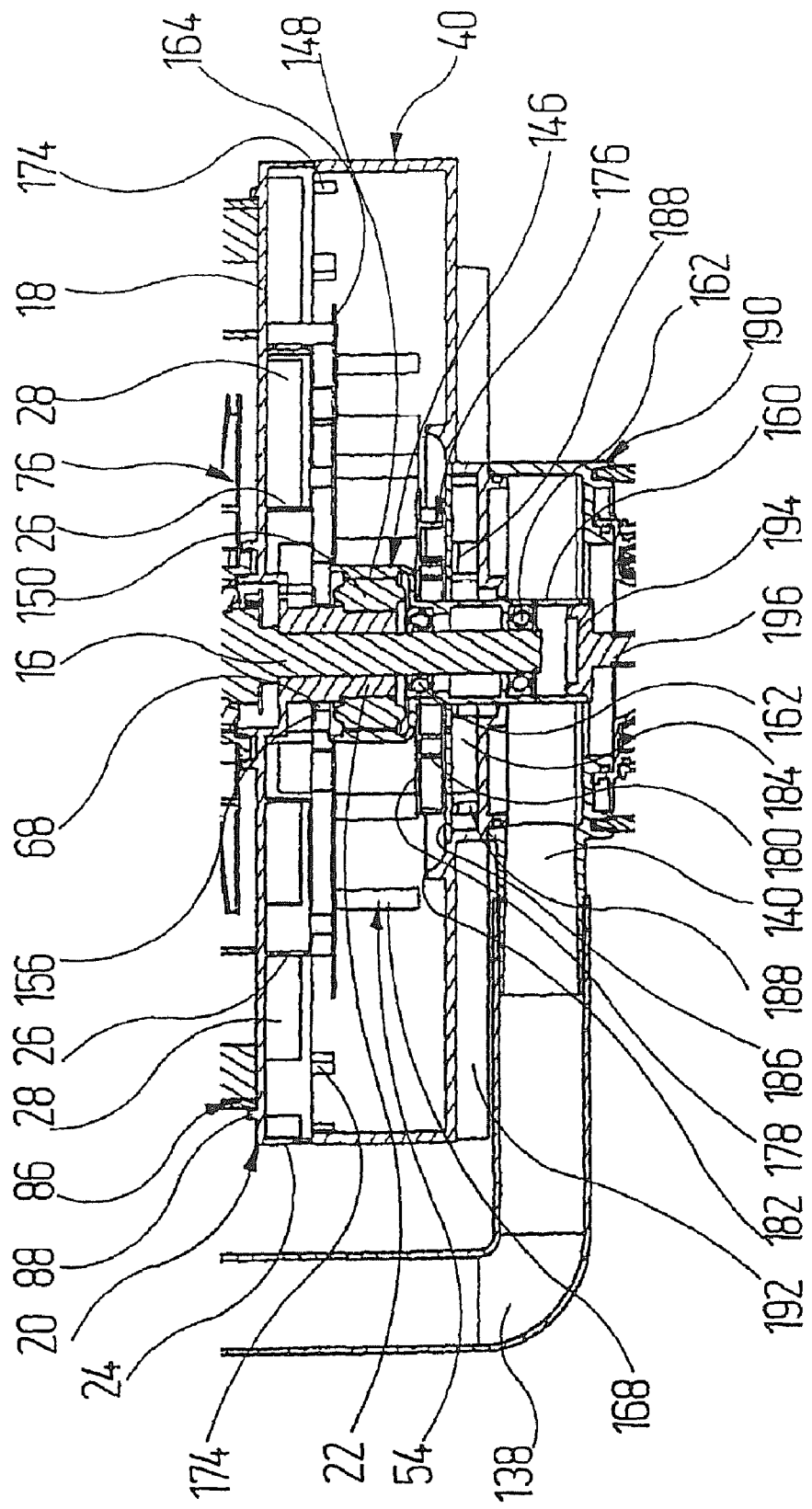
FIG. 6 is an axial section through a central electronics and ventilator unit of the suction fan according to FIG. 1 and through the drive motor for the centrifugal separator of the suction fan according to FIG. 1.

While this invention is susceptible of embodiment in many different forms, there is shown in the drawings and will herein be described in detail one or more embodiments with the understanding that the present disclosure is to be considered as an exemplification of the principles of the invention and is not intended to limit the invention to the embodiments illustrated Shown in FIGS. 1 to 7 is a dental suction fan, provided overall with the reference symbol 10. The suction fan 10 include a radial fan 12, at the top in FIGS. 1 to 3, to which a centrifugal separator 14, at the bottom in FIGS. 1 to 3, is firmly connected.

The radial fan 12 and the centrifugal separator 14 are arranged in series with respect to an axle 16, which is fixed with respect to the housing and which in FIG. 1 extends vertically, in substantially rotationally symmetrical manner and coaxially relative to the axle 16 which is fixed with respect to the housing.

The axle 16 which is fixed with respect to the housing leads centrically through a circular, flat supporting plate 18 of a supporting housing provided overall with the reference symbol 20. The axle 16 which is fixed with respect to the housing is shrink-fitted into a rotationally symmetrical carrying socket 22 which is integrally moulded onto the supporting plate 18 and which is located on the side of the supporting plate 18 facing towards the centrifugal separator 14.

A cylindrical peripheral wall 24 which is open towards the centrifugal separator 14—that is to say, in the downward direction—is circumferentially moulded onto the edge of the supporting plate 18.

On the side facing towards the centrifugal separator 14 furthermore two circular cylindrical reinforcing ribs 26, coaxial in relation to the axle 16 which is fixed with respect to the housing, are moulded onto the supporting plate 18. The axial extent of the reinforcing ribs 26 corresponds to the axial extent of the peripheral wall 24. Between the circular reinforcing ribs 26, and between the outer circular reinforcing rib 26 and the peripheral wall 24, there extend a plurality of radially extending transverse ribs 28.

The supporting housing 20 is manufactured from aluminium by a die-casting process. But it may also be produced in some other way.

Overall, the supporting housing 20 and the axle 16 which is fixed with respect to the housing form a stable skeleton for the dental suction fan 10.

The radial fan 12 is located on the side of the supporting plate 18 facing away from the centrifugal separator 14. On that side the axle 16 which is fixed with respect to the housing exhibits a stator-carrying region 30 with a widened cross-section. The stator-carrying region 30 is located in the axial direction, at a spacing from the upper front face of the carrying socket 22. The outside diameter of the stator-carrying region 30 corresponds to the outside diameter of the carrying socket 22.

The upper front face of the carrying socket 22 forms the bottom of a circular cylindrical motor chamber 32 which is coaxial relative to the axle 16 fixed with respect to the housing and which is located in the centre of the supporting plate 18. The peripheral side of the motor chamber 32 merges integrally, approximately in its axial centre, with the supporting plate 18. The stator-carrying region 30 of the axle 16 which is fixed with respect to the housing extends in the axial direction approximately over one quarter of the total length of the axle 16 which is fixed with respect to the housing—that is to say, approximately over one half of the axial height of the radial fan 12.

The axle 16 which is fixed with respect to the housing is provided, adjacent to the stator-carrying region 30, with a cylindrical axial bore 34 which is open towards the front side of the axle 16 fixed with respect to the housing, which faces away from the centrifugal separator 14. A little downstream of the stator-carrying region 30 the axle 16 which is fixed with respect to the housing exhibits a transverse bore 36 which leads from the generated surface of the axle to the bore 34.

By means of a throttle screw 37, which co-operates with an opening 64 situated above the end of the bore 34 (FIG. 8), a stream of cooling air through the interior of the upper end section of the shaft 16 can be adjusted, the generation of which is described further below.

The bottom of the circular cylindrical motor chamber 32 exhibits moreover a plurality of uninterrupted air slits 38. Through the air slits 38, air is able to flow out of a electronics housing 40, which is located on the side of the supporting plate 18 facing towards the centrifugal separator 14, into the motor chamber 32.

On the peripheral surface of the stator-carrying region 30 of the axle 16 which is fixed with respect to the housing a number of stator cores 42 are seated which constitute part of a fan drive motor designated overall by 44. The stator cores 42 include a plurality of metal sheets. The metal sheets carry windings 46 which are distributed in the circumferential direction and illustrated in FIG. 4. In exemplary manner in FIG. 4 only two of the windings 46 are shown, which are connected to a commutator plate 50 via respective connecting lines 48. The commutator plate 50 is connected via two supply lines 52 in each instance to a pole of a voltage output of a control unit 54. Given appropriate application of current to the windings 46 by the control unit 54, the stator cores 42 generate a rotating field.

On the fan side a rotor bell 56 made of steel for the fan drive motor 44 is rotatably arranged on the axle 16 which is fixed with respect to the housing. The rotor bell 56 rotates in the axial direction towards the centrifugal separator 14, viewed in the clockwise direction.

Moulded onto the rotor bell 56 on the side facing away from the centrifugal separator 14, coaxially relative to the rotor bell 56, is a circular cylindrical bearing housing 58 having a smaller diameter than that of the rotor bell 56. In the bearing housing 58 two axially spaced bearings 60 are arranged, via which the rotor bell 56 is supported in the region of the upper end of the axle 16 which is fixed with respect to the housing.

The upper front end of the bearing housing 58 of the fan drive motor 44 is sealed with a cap 62 which is convex, viewed from the outside. The cap 62 exhibits centrically an opening 64 for cooling air, which emerges at the front end from the bore 34 of the axle 16 which is fixed with respect to the housing. By means of the cap 62, the bearings 60 of the fan drive motor 44 are largely encased. The opening 64 enables a metered escape of the cooling air and ensures a good cooling of the bearings 60.

The rotor bell 56 is open towards the centrifugal separator 14. On its interior peripheral surface it bears a plurality of high-performance magnet segments 66 distributed in the peripheral direction or an annular magnet which is provided with a plurality of magnetisations alternating in the peripheral direction.

On the radial annular surface of the stator-carrying region 30 facing towards the centrifugal separator 14 there is seated furthermore the commutator plate 50 with three Hall-effect generators 68, with which, in known manner, the fan drive motor 44 is operated in electrically commutated manner.

The commutator plate 50 of the fan drive motor 44 is laterally recessed, so that cooling air, which flows in from the electronics housing 40 through the air slits 38 in the region of the carrying socket 22, is able to flow past the commutator plate 50 to the stator cores 42. Furthermore, the supply lines 52 from the control unit 54 are also fed through there.

The rotor bell 56 for the fan drive motor 44 is arranged on the axle 16 which is fixed with respect to the housing in such a way that an annular gap 72 remains between the stator cores 42 and the radial annular surface facing towards the bearing housing 58 of the rotor bell 56. The transverse bore 36, which comes from the bore 34 of the axle 16 which is fixed with respect to the housing, communicates with the annular gap 72.

Between the stator cores 42 and the high-performance magnet segments 66 there is, as stated, a narrow annular gap, through which cooling air is able to flow in the axial direction.

A first impeller 74 of the radial fan 12 is seated on the bearing housing 58 of the rotor bell 56; a second impeller 76 is seated on the lower end of the rotor bell 56. The impellers 74 and 76 are screw-coupled, in each instance with the aid of three metal screws which are not shown in FIGS. 1 to 3, with the peripheral wall of the rotor bell 56 and with the bearing housing 58, respectively. The metal screws are secured with adhesive.

The impellers 74 and 76 each include a flat, high-strength wheel disc 78, at the bottom in FIG. 1, with moulded-on wheel blades 80 which are concavely curved contrary to the direction of rotation of the impellers 74 and 76. The wheel discs 78 are injection-moulded from plastic and reinforced with glass fibre. On account of their curvature, the wheel blades 80 are streamlined and quiet.

The edges of the wheel blades 80 that are remote from the wheel disc 78 are covered in each instance by a front disc 82, said front discs extending in the radial direction as far as the outer edges of the wheel blades 80 and the outer edges of the wheel discs 78, radially aligned with said outer edges of said wheel blades. In the radially inward direction the front discs 82 protrude beyond the radially inner ends of the wheel blades 80.

The front discs 82 are made of a hard aluminium alloy of low density. Alternatively, the front discs 82 may be made of plastic that has the same coefficient of expansion as the plastic from which the wheel discs 78 are manufactured.

The front discs 82 are connected to the wheel blades 80 by means of hot riveting or ultrasonic riveting.

At the edge situated radially on the inside, the front discs 82 have an axially short inlet nozzle 84 which merges, with a generously dimensioned external curvature, with the axially outer surface which is inclined in relation to the wheel disc 78 that is to say, which is frustoconical. In radially outwards the front disc 82 tapers to the wheel disc 78.

The second impeller 76 is located in an impeller chamber in the centre of a cup-shaped housing segment 86 which is open towards the supporting plate 18 and which in its cover part has an opening for the rotor bell 56. The outside diameter of the housing segment 86 is somewhat smaller than the outside diameter of the supporting plate 18. The peripheral wall of the housing segment 86 bears closely, at its free edge with its outer peripheral surface, against the inside of a circular positioning bar 88. The positioning bar 88 is integrally moulded onto the surface of the supporting plate 18 facing towards the radial fan 12.

In the housing segment 86, the second impeller 76 conveys air into a helical outlet channel 90 which is delimited by a helical wall section at the edge of the housing segment 86, widening in the outlet direction, and by a helical edge wall 92. The helical shape of the outlet channel 90 is logarithmic. But the outlet channel 90 may also be configured in a different manner in such a way that the air flowing through it has a constant swirl.

The wall section communicates with an outlet nozzle 94 (see FIG. 3) which is tangential to the outlet channel 90. The edge wall 92 depends from the upper cover part of the housing segment 86.

An interspace between the helical outlet channel 90 and the radially outer side wall of the housing segment 86 is filled with an insulating foam 96 for the purpose of acoustic insulation.

The radially inner edge of the upper cover part of the housing segment 86 is generously bent by 90° axially inwards towards the supporting plate 18. In the axial direction it overlaps, radially from outside, the inlet nozzle 84 of the second impeller 76, retaining a clearance.

Moulded onto the upper side of the upper cover part of the housing segment 86 facing away from the supporting plate 18 is a lower deflecting stepped wall 98 which is rotationally symmetrical to the axle 16 which is fixed with respect to the housing.

The inside—which is concavely curved, viewed radially from the inside—of the lower deflecting stepped wall 98 has the shape of a quadrant in axial section. The upper side of the upper cover part of the housing segment 86 merges tangentially with the inside of the lower deflecting stepped wall 98.

The upper edge of the lower deflecting stepped wall 98 facing away from the housing segment 86 is situated in the axial direction somewhat below the annular surface between the bearing housing 58 and the rotor bell 56 of the fan drive motor 44. The radially outer wall of the lower deflecting stepped wall 98 extends in circular cylindrical manner coaxially relative to the axle 16 which is fixed with respect to the housing. It is aligned in the axial direction approximately with the radially outer boundary of the helical outlet channel 90 in the housing segment 86.

In the radial direction there is aligned with the upper edge of the lower deflecting stepped wall 98 an underside, facing towards the supporting plate 18, of a flat guide element 100 which is rotationally symmetrical to the axle 16 which is fixed with respect to the housing. The edge of the guide element 100 is cut away in axial section in streamlined manner in the shape of a semicircular arc. The diameter of the guide element 100 corresponds approximately to the inside diameter of the lower deflecting stepped wall 98 in the region of its tangential transition to the upper side of the upper cover part of the housing segment 86.

In its centre the guide element 100 is provided with an uninterrupted opening for the rotor bell 56, which is rotationally symmetrical to the axle 16 which is fixed with respect to the housing. On the underside of the guide element 100 facing towards the supporting plate 18 the opening is adjoined by a collar 102, the circular cylindrical inner surface of which, which is coaxial relative to the axle 16 which is fixed with respect to the housing, surrounds the rotor bell 56, retaining a clearance. The outer surface of the collar 102 in the radial direction merges in streamlined curved manner, in the shape of a quadrant arc in axial section, with the horizontal underside of the guide element 100 facing towards the housing segment 86.

From the underside of the guide element 100 there depend swirl blades 104, moulded onto said underside, which are curved contrary to the curvature of the wheel blades 80 of the impellers 74 and 76.

The edges of the swirl blades 104 that are remote from the guide element 100 bear in gap-free manner against the flat region of the upper side of the cover part of the housing segment 86. The radially inner edges of the swirl blades 104 reach as far as the transition of the flat region of the underside of the guide element 100 into the bend of the outer surface of the collar 102.

On the housing segment 86 there is seated an intake housing segment 106 which is rotationally symmetrical to the axle 16 which is fixed with respect to the housing. The outside diameter of the intake housing segment 106 corresponds roughly to the outside diameter of the housing segment 86. The edge of the outer wall of the intake housing segment 106 facing towards the housing segment 86 exhibits a radially internal step which overlaps the upper edge of the housing segment 86, and in this way the intake housing segment 106 is held in non-slip manner in the radial direction in relation to the housing segment 86.

A false bottom 108 of the intake housing segment 106 is located on the side of the guide element 100 situated opposite the housing segment 86, and delimits with said guide element an impeller chamber in which the first impeller 74 rotates.

Integrally moulded onto the underside of the false bottom 108 facing towards the housing segment 86 is an upper deflecting stepped wall 110, the free edge of which bears closely against the free edge of the lower deflecting stepped wall 98. The contour of the radially inner surface of the lower deflecting stepped wall 98 merges in stepless manner with the corresponding contour of the upper deflecting stepped wall 110. The radially inner surface of the upper deflecting stepped wall 110 is curved in axial section, in a manner analogous to the lower deflecting stepped wall 98, so as to correspond to a quadrant arc, the radius of which, however, is distinctly smaller than the radius of the corresponding quadrant arc of the lower deflecting stepped wall 98. The deflecting stepped walls 98 and 110 together form a deflecting stage which conducts air from the radially external discharge region of the first fan stage to the radially internal intake region of the second fan stage.

The radially inner surface of the upper deflecting stepped wall 110 merges tangentially with an annular horizontal region of the false bottom 108 of the intake housing segment 106.

In the radial direction, approximately aligned with the outer edges of the first impeller 74, the annular horizontal outer region of the false bottom 108 in the radially inward direction is adjoined by an approximately conical region which ascends in the radial direction towards the axle 16 which is fixed with respect to the housing. The conical region of the false bottom 108 is set somewhat more steeply than the front disc 82 of the first impeller 74.

In its centre the conical region of the false bottom 108 exhibits a passage opening for the inlet nozzle 84 of the first impeller 74.

The radially inner edge of the false bottom 108 is shaped into an inlet funnel 112a. For this purpose the false bottom 108 is firstly bent in the shape of a circular cylinder away from the supporting plate 18 and, above the free edge of the inlet nozzle 84, is guided back downwards in the direction of the supporting plate 18 in the shape of a funnel with a generous bend. The circular cylindrical inner edge region of the false bottom 108 encloses the inlet nozzle 84 of the first impeller 74, retaining a clearance.

The guide element 100 further exhibits, in its surface facing towards the first impeller 74, a flat recess 112, circular in top view, for the wheel disc 78 of the first impeller 74, which is guided out in the radial direction via the outer edge of said impeller. In the radial direction, approximately aligned with the centre of the bent surface of the collar 102 on the underside of the guide element 100, a circumferential bar 114, projecting axially upwards, is moulded on in the recess 112. While retaining a clearance, the bar 114 reaches as far as the front disc 82 of the first impeller 74.

Furthermore, on the upper side of the guide element 100 in the region outside the recess 112 a guide ring is arranged which surrounds the first impeller 74. The guide ring consists of a plurality of guide blades 116 which are fixed with respect to the housing and which constitute secants, not intersecting the axle 16 which is fixed with respect to the housing, of the inner contour of the guide element 100. The guide blades 116 extend in the radially inward direction up to a short distance before the recess 112 in the guide element 100. In the radially outward direction the guide blades 116 extend as far as the outer edge of the guide element 100. The guide blades 116 are set contrary to the swirl of the air that is output by the first impeller 74. They constitute, at the same time, spacers for the guide element 100 and for the radial false bottom 108 of the intake housing segment 106.

An annular space—which is delimited by the radial outsides of the deflecting stepped walls 98 and 110, by the associated peripheral wall of the intake housing segment 106 and by the associated regions of the false bottom 108 and of the housing segment 86—is filled with an insulating foam 118 for the purpose of acoustic insulation.

Located above the false bottom 108 is an inflow space 120 which is sealed on the side facing away from the centrifugal separator 14 by a ribbed plastic cover 122. The ribs of said plastic cover are located on the surface of the plastic cover 122 facing away from the inflow space 120.

The plastic cover 122 exhibits in the centre a dome-shaped elevation for the cap 62 of the rotor bell 56 of the radial fan 12. In this manner, the outflowing cooling air of the bearings 60 is able to flow past into the inflow space 120 in a gap between the plastic cover 122 and the cap 62.

The plastic cover 122 is provided on its peripheral side with four screw lugs 124 arranged in the form of a cross, which are shown in FIG. 3. The screw lugs 124 are aligned in the axial direction with four corresponding threaded bores 126 in the supporting plate 18. A threaded bolt, not shown in FIG. 3, is passed through each screw lug 124 and is screw-coupled in the threaded bore 126 of the supporting plate 18. In this manner, the intake housing segment 106 and the housing segment 86 are fixed in the axial direction between the plastic cover 122 and the supporting plate 18.

Located in the inflow space 120 is an approximately circular cylindrical wall 128 which is interrupted in the peripheral direction and which extends coaxially relative to the axle 16 which is fixed with respect to the housing from the upper side of the false bottom 108 not quite as far as the underside of the plastic cover 122.

At equal intervals the wall 128 exhibits approximately twelve apertures 130 which are square, viewed in the radial direction. The apertures 130 extend in the axial direction over virtually the entire height of the wall 128 and are open on the side facing towards the false bottom 108. The width of the apertures 130 in the peripheral direction is somewhat smaller than the width of the regions of the wall 128 that have been left standing.

The diameter of the wall 128 corresponds approximately to the diameter of the first impeller 74. On a peripheral side the wall 128 has an inflow opening 132 which is square in the radial direction and which has approximately the width of the apertures. The inflow opening 132 is delimited on both sides by, in each case, a plate 134, said plates jointly forming—in each instance half of the periphery—the wall 128, and being half bent outwards perpendicular to the wall 128.

The inflow opening 132 is aligned in the radial direction with a connecting nozzle 136 which is borne by the peripheral wall of the intake housing segment 106. Fitted onto the connecting nozzle 136 from outside is connecting pipe 138. The connecting pipe 138 comes from an air outlet nozzle 140 of the centrifugal separator 14.

An annular space, which is delimited by the peripheral wall of the intake housing segment 106 in the region of the inflow space 120 and by the wall 128 and is interrupted between the inflow opening 132 and the opening of the connecting nozzle 136, is filled with insulating foam 142.

In the radial direction between the inlet funnel 112a of the first impeller 74 and the inflow opening 132 a jet-splitting wall 144 is arranged which is V-shaped in axial view; the point of the V points towards the inflow opening 132. The jet-splitting wall 144 extends over the entire axial height of the inflow space 120.

The jet-splitting wall 144 serves for splitting the airstream flowing from the connecting pipe 138 to the inflow space 120 into two airstream parts flowing with opposite swirl. The cooperation of the jet-splitting wall 144 with the wall 128 exhibiting the apertures 130 brings about overall a swirl-free inflow of air into the inlet nozzle 84 of the first impeller 74.

A separator drive motor 146 is constructed in a manner analogous to the fan drive motor 44. It exhibits a rotor bell 148 which is supported on the end section of the axle 16 fixed with respect to the housing that faces away from the radial fan 12. The rotor bell 148 rotates in the axial direction towards the centrifugal separator 14, viewed in the clockwise direction.

The free edge of the rotor bell 148 is located at a generous spacing from an imaginary plane in which the free lower edges of the reinforcing ribs 26 of the supporting housing 20 are situated.

On the inside of the rotor bell 148, as in the case of the rotor bell 56 of the fan drive motor 44, high-performance magnet segments are affixed circumferentially, which in FIG. 1 are covered.

Appropriate stator cores 150 are fastened to the radial outside of the carrying socket 22. A plurality of windings 152, shown schematically in FIG. 4, of the stator cores 150 of the separator drive motor 146 are connected via connecting lines 154 to a commutator plate 156, and the latter is connected to the control unit 54 via supply lines 158. The windings 152 of the separator drive motor 146 are capable of being independently supplied with current by the control unit 54 independently of the windings 46 of the fan drive motor 44 via separate supply circuits, in particular with supply currents exhibiting differing frequencies.

The commutator plate 156 is fastened on the side of the stator cores 148 of the separator drive motor 146 on the carrying socket 22 facing towards the supporting plate 18 in the axial direction. It exhibits three Hall-effect generators 68 for the separator drive motor 146 and works in accordance with the commutator plate 50 of the fan drive motor 44.

On the front side facing towards the centrifugal separator 14 the rotor bell 148 of the separator drive motor 146 exhibits a bearing housing 160 which is coaxial relative to the axle 16 which is fixed with respect to the housing.

In the bearing housing 160 two axially spaced bearings 162 are arranged which are retained by the carrying socket 22 coaxially relative to the axle 16 which is fixed with respect to the housing.

The rotor bell 148 of the separator drive motor 146 is located in the electronics housing 40 which is rotationally symmetrical to the axle 16 which is fixed with respect to the housing, said electronics housing having the same diameter as the supporting plate 18.

The electronics housing 40 is cup-shaped and sealed towards the radial fan 12 with the supporting plate 18. The edge of the electronics housing 40 rests upon the edge of the supporting plate 18 and is firmly connected to said edge. The bottom of the electronics housing 40 is located between the two bearings 162 of the separator drive motor 146, close to the bearing 162 facing towards the supporting plate 18.

The electronics housing 40 is made of metal, so that in conjunction with the supporting housing 20 made of aluminium it acts as shielding in relation to electric, magnetic and electromagnetic fields.

In the radial direction, aligned with the edge of the rotor bell 148, an annular electronics plate 164 is arranged coaxially relative to the axle 16 which is fixed with respect to the housing. The electronics plate 164 is suspended, at a spacing from the reinforcing ribs 26 of the supporting housing 20, on attachment cylinders 166 on the underside of the supporting plate 18. On the underside facing away from the supporting plate 18 the electronics plate 164 bears a plurality of microprocessors, power semiconductors and other electronic components, equally denoted by reference symbol 168, which jointly form the control unit 54. Furthermore, the control unit 54 exhibits a power pack 170 shown in FIG. 4, with which the requisite DC voltages can be generated from the mains voltage. In addition, a power cable 172 shown in FIG. 4 leads to the control unit 54.

In the region of its edge adjoining the supporting plate 18 the electronics housing 40 exhibits in its peripheral wall a plurality of exhaust-air openings 174. Through the exhaust-air openings 174, warmed air for cooling the microprocessors, power semiconductors and the other electronic components 168 is able to escape from the electronics housing 40.

Fitted on the radial outside of the bearing housing 160 of the separator drive motor 146 is a ventilator wheel 176 for cooling the electronics housing 40. A ventilator wheel disc 178 of the ventilator wheel 176 bears against the front side of the rotor bell 148 facing towards the centrifugal separator 14. Its diameter is distinctly smaller than the diameter of the wheel discs 78 of the two impellers 74 and 76.

The impellers 74 and 76, the rotor bells 56 and 148 and the ventilator wheel 176 are each dynamically counterbalanced in at least two balancing planes. In order to reduce the effort, the individual components are statically counterbalanced prior to assembly of the dental suction fan 10.

On the side facing away from the rotor bell 148, concavely curved wheel blades 180 are moulded onto the ventilator wheel disc 178 contrary to the direction of rotation of the rotor bell 148. The edges of the wheel blades 180 that are remote from the ventilator wheel disc 178 point downwards to the centrifugal separator 14. The wheel blades 180 terminate in the axial direction just above the upper side of the bottom of the electronics housing 40.

The ventilator wheel 176 is surrounded by a circumferential guide rib 182 which is rotationally symmetrical to the axle 16 which is fixed with respect to the housing and which exhibits approximately the shape of the lower deflecting stepped wall 98 elucidated above. The guide rib 182 is integrally moulded onto the upper side of the bottom of the electronics housing 40.

In the centre of the guide rib 182 the bottom of the electronics housing 40 is lowered several times in step-like manner and forms there a cooling-air intake space 184. The cooling-air intake space 184 is sealed on the ventilator-wheel side with a ring plate 186. An air gap is situated between the inner edge of the ring plate 186 and the outer peripheral side of the bearing housing 160 of the rotor bell 148.

The peripheral wall of the cooling-air intake space 184 exhibits at the top, close to the ring plate 186, a plurality of intake openings 188 for cooling air.

The bearing housing 160 of the separator drive motor 146 leads though an opening in the bottom of the cooling-air intake space 184 into an outlet housing segment 190 of the centrifugal separator 14, retaining a clearance.

Moulded in addition onto the underside of the electronics housing 40 are a plurality of stabilising ribs 192 extending in the radial direction.

The cup-shaped outlet housing segment 190 which is substantially rotationally symmetrical to the axle 16 which is fixed with respect to the housing is made of plastic and adjoins the cooling-air intake space 184 in the axial direction. The outlet housing segment 190 is tightly sealed at the top by the bottom of the cooling-air intake space 184. The air outlet nozzle 140, on which the connecting pipe 138 is placed, leads laterally out of the outlet housing segment 190.

Into the open front side of the bearing housing 160 of the separator drive motor 146 facing away from the rotor bell 148 a drive plate 194 which is coaxial relative to the axle 16 which is fixed with respect to the housing is inserted and is fixed there. Moulded onto the drive plate 194 is a separator shaft 196 made of stainless steel, which is coaxial relative to the axle 16 which is fixed with respect to the housing.

Fastened to the separator shaft 196 are several pump vanes 198 of a discharge-pump wheel and a guide wall 200 of a cyclone chamber, the latter via several radial air-rotation vanes 202 which are firmly borne by the separator shaft 196. The aforementioned parts 198, 200 and 202 consequently rotate together with the separator shaft 196.

A little below the outlet housing segment 190 there is furthermore located, according to FIGS. 2 and 3, in the peripheral wall of the centrifugal separator 14 an inlet nozzle 206 to which a tube is attached, via which a mixture of air and secretion, which is to be separated and purified, is conducted into the centrifugal separator 14. At the bottom the centrifugal separator 14 exhibits a connecting nozzle 204 for a waste-water line which is not shown.

The centrifugal separator 14 and its mode of operation are known, incidentally, from DE 100 10 077 A1.

The dental suction fan 10 operates as follows:

With the control unit 54 the windings 46 and 152 of the fan drive motor 44 and of the separator drive motor 146, respectively, are supplied with current separately from one another, and in this way the respective rotor bell 56 and 148 is driven. The fan drive motor 44 is preferentially regulated to a rotational speed between 10,000 and 14,000 revolutions per minute; the separator drive motor 146 preferentially to a rotational speed between 3000 and 4000 revolutions per minute.

The fan drive motor 44 drives the impellers 74 and 76 in the same direction of rotation and at the same rotational speed.

By virtue of the rotation of the first impeller 74, an underpressure is generated which acts via the inflow space 120 and the connecting pipe 138 in the outlet housing segment 190 of the centrifugal separator 14. With the underpressure predetermined by the control unit 54, the mixture of air and secretion is sucked via the pipe and the inlet nozzle 206 into the centrifugal separator 14, and from there into the cyclone chamber.

By virtue of the rotation of the separator drive motor 146, via the separator shaft 196 the guide wall 200 of the cyclone chamber is rotated, so that a separation of the water and of the contained solids from the air occurs in known manner, both in accordance with the cyclone principle and in accordance with the centrifugal principle.

The waste water with the contained solids is conveyed with the pump vanes 198 of the discharge pump, which is driven via the separator shaft 196 by the separator drive motor 146, into the waste-water line via the connecting nozzle 204.

The purified air, which is free from solid and liquid constituents, is subsequently sucked upwards into the outlet housing segment 190. From there it flows, following the underpressure, via the connecting pipe 138 to the inflow space 120.

In the inflow space 120 the airstream is split, as already described, by the jet-splitting wall 144, and flows in swirl-free manner via the inlet nozzle 84 of the first impeller 74 to the interior of this impeller 74. The wheel blades 80 accelerate the air outwards and in this way bring about an underpressure at the inlet nozzle 84.

The accelerated air is supplied via the deflecting stepped walls 110 to the inlet nozzle 84 of the second impeller 76, where it is accelerated further via the wheel blades 80 and is guided outwards into the outlet channel 90. Via the outlet nozzle 94 the air is blown under pressure into the environment.

At the same time, driven by the separator drive motor 146, with the ventilator wheel 176 cooling air is aspirated through the intake openings 188 in the electronics housing 40.

The cooling air flows over the thermally loaded electronic components 168 on the electronics plate 164 and cools them.

Some of the warmed cooling air flows away through the exhaust-air openings 174 of the electronics housing 40.

The remainder of the warmed cooling air flows through the air slits 38 in the carrying socket 22 into the motor chamber 32 of the fan drive motor 44, which is situated above the electronics plate 164.

The cooling air flows past the gap in the electronics plate 164 to the stator cores 42 and cools the latter.

From there, the cooling air flows through the transverse bore 36 above the stator cores 42 into the bore 34 in the axle 16 which is fixed with respect to the housing.

The cooling air flows through the bore 34 in the axial direction and in this way cools the two bearings 60 of the fan drive motor 44 from the inside.

The cooling air flows out of the front side of the axle 16 which is fixed with respect to the housing into the region below the cap 62 and from there through the opening 64 into the inflow space 120, where it mixes with the main airstream, described above, consisting of purified air, and is ultimately conducted away to the environment with said air.

In the exemplary embodiment of a dental suction fan 10 described above, inter alia the following modifications are possible:

The control unit 54 may additionally simply be connected to optical and/or acoustic output means, for example to warning indications and illuminated displays or hooters. In addition, the control unit 54 may exhibit memory means in which data characterising the operation of the dental suction fan 10 can be stored which may, for example, contain information about the cycle of operation or the service life of the dental suction fan 10. These data may, for example, be retrieved for repair and for maintenance purposes.

Instead of regulating the rotational speeds of the fan drive motor 44 and/or the separator drive motor 146 in each instance to a constant rotational speed, the rotational speeds may also be regulated in pressure-led manner with the control unit 54. For this purpose, additionally a pressure sensor may be provided, with which the underpressure prevailing in the connecting nozzle 206 can be ascertained and passed on to the control unit 54.

Instead of an motor arrangement that exhibits two independently running rotors on a common axle, use may also be made of two independent motors that are situated axially in series and are connected via their housings or that have preferentially cup-shaped housings that are fastened to the two sides of the supporting plate 18 by their end faces that are remote from the shafts. Such independent motors may then also be standard internal-rotor motors It is again emphasized that the above-described embodiments of the present invention, particularly, any "preferred" embodiments, are possible examples of implementations merely set forth for a clear understanding of the principles of the invention. Many variations and modifications may be made to the above-described embodiments of the invention without substantially departing from the spirit and principles of the invention. All such modifications are intended to be included herein within the spirit of the invention and the scope of protection is only limited by the accompanying claims.

The invention claimed is:

1. A suction device for dental, medical and industrial purposes comprising:
   a radial fan which exhibits a suction side and a pressure side;
   a centrifugal separator, an air outlet of which is connected to the suction side of the radial fan;
   at least one drive unit which includes an electric motor and serves for driving the radial fan and the centrifugal separator; and,
   a control unit for the drive unit, wherein
   the drive unit includes a fan drive motor and a separator drive motor, which are arranged in series, rotationally decoupled, and drive the radial fan and the centrifugal separator, respectively, and wherein
   the fan drive motor and the separator drive motor have a common axle which is fixed with respect to a housing, and
   the fan drive motor includes a stator which is seated on a peripheral surface of the common axle, and the separator drive motor has a stator which is fastened to a radial outside of a carrying socket which is fastened to the common axle, and the fan drive motor includes a rotor with bearings and the separator drive motor includes a rotor with bearings and wherein the fan drive motor bearings and the separator drive motor bearings are carried by the common axle.

2. The suction device of claim 1, wherein the respective stators being connected to the axle, and rotating parts of the radial fan being connected in non-rotating manner to the rotor of the fan drive motor and rotating parts of the centrifugal separator being connected in non-rotating manner to the rotor of the separator drive motor and being supported in rotating manner coaxially relative to the common axle.

3. The suction device of claim 2, wherein the rotors each take the form of a rotor bell wherein each rotor bell is carrying magnet segments on their inside and each rotor bell is placed from one end onto the common axle which is fixed with respect to the housing.

4. The suction device of claim 1, wherein the fan drive motor and the separator drive motor are electronically commutated.

5. The suction device of to claim 4, wherein the fan drive motor and the separator drive motor each exhibit a commutator plate with three magnetic-field transducers and the commutator plates are mounted on the axle which is fixed with respect to the housing.

6. The suction device of claim 1, wherein the radial fan comprises a first stage and a second stage each comprising an impeller revolving in a working space a deflecting stage being coaxially arranged on the common axle between the first stage and the second stage connecting an outlet of the first stage to an inlet of the second stage.

7. The suction device of claim 2, wherein the common axle exhibits a cavity extending in direction, which is provided with uninterrupted inlet connections and output connections for cooling air to a circumferential surface and to a front side of the common axle, respectively.

8. The suction device according to claim 1, wherein the fan drive motor and the separator drive motor are synchronous motors and their supply circuits provide supply signals with differing frequencies.

9. The suction device of claim 1, wherein the control unit is accommodated in a disc-shaped housing part, the radial dimension of which corresponds substantially to that of the radial fan.

10. The suction device of claim 1, wherein a housing of the radial fan has an outer wall which is covered at least partly with insulating material.

11. The suction device of claim 2, wherein the fan drive motor and the separator drive motor are electronically commutated.

12. The suction device of claim 11, wherein the fan drive motor and the separator drive motor each exhibit a commutator plate with three magnetic-field transducers and the commutator plates are mounted on the axle which is fixed with respect to the housing.

13. The suction device of claim 2, wherein the radial fan comprises a first stage and a second stage each comprising an impeller in a working space, and a deflecting stage being coaxially arranged between the first stage and the second stage connecting an outlet of the first stage to an inlet of the second stage.

14. The suction device of claim 2, wherein a ventilator wheel for cooling thermally loaded components of the suction device including the control unit, the stators and/or the bearings of the rotors is coaxially arranged on the common axle between the fan drive motor and the separator drive motor, the ventilator wheel being driven by the fan drive motor or the separator drive motor.

15. The suction device of claim 2, wherein the common axle exhibits a cavity extending in a longitudinal direction, which is provided with uninterrupted inlet connections and output connections for cooling air to a circumferential surface and to a front side of the common axle, respectively.

16. The suction device of claim 2, wherein the control unit is arranged in a region between the fan drive motor and the separator drive motor.

17. A suction device for dental, medical and industrial purposes comprising:
 a radial fan which exhibits a suction side and a pressure side;
 a centrifugal separator, an air outlet of which is connected to the suction side of the radial fan;
 at least one drive unit which includes an electric motor and serves for driving the radial fan and the centrifugal separator; and,
 a control unit for the drive unit, wherein
 the drive unit includes a fan drive motor and a separator drive motor, which are arranged in series, rotationally decoupled, and drive the radial fan and the centrifugal separator, respectively, and,
 wherein the fan drive motor and the separator drive motor have a common axle which is fixed with respect to a housing, and,
 wherein the fan drive motor includes a stator which is seated on a peripheral surface of the common axle, and,
 wherein the separator drive motor has a stator which is fastened to a radial outside of a carrying socket which is fastened to the common axle, and,
 wherein the fan drive motor includes a rotor with bearings and a rotor bell rotatably arranged on a first end portion of the common axle, and,
 wherein the separator drive motor includes a rotor with bearings and a rotor bell rotatably arranged on a second end portion of the common axle,
 and wherein the fan drive motor bearings and the separator drive motor bearings are carried by the common axle.

18. A suction device for dental, medical and industrial purposes comprising:
 a radial fan which exhibits a suction side and a pressure side;
 a centrifugal separator, an air outlet of which is connected to the suction side of the radial fan;
 at least one drive unit which includes an electric motor and serves for driving the radial fan and the centrifugal separator; and,
 a control unit for the drive unit, wherein
 the drive unit includes a fan drive motor and a separator drive motor, which are arranged in series, rotationally decoupled, and drive the radial fan and the centrifugal separator, respectively, and wherein
 the fan drive motor and the separator drive motor have a common axle which is fixed with respect to a housing, and
 the fan drive motor includes a stator which is seated on a peripheral surface of the common axle, and
 the separator drive motor has a stator which is fastened to a radial outside of a carrying socket which is fastened to the common axle, and
 the fan drive motor includes a rotor with bearings and the separator drive motor includes a rotor with bearings and wherein the fan drive motor bearings and the separator drive motor bearings are carried by the common axle; and, wherein a ventilator wheel for cooling thermally loaded components of the suction device including the control unit, the stators and/or the bearings of the rotors is coaxially arranged on the common axle between the fan drive motor and the separator drive motor, the ventilator wheel being driven by the fan drive motor or the separator drive.

19. A suction device for dental, medical and industrial purposes comprising:

a radial fan which exhibits a suction side and a pressure side;

a centrifugal separator, an air outlet of which is connected to the suction side of the radial fan;

at least one drive unit which includes an electric motor and serves for driving the radial fan and the centrifugal separator; and, a control unit for the drive unit, wherein the drive unit includes a fan drive motor and a separator drive motor, which are arranged in series, rotationally decoupled, and drive the radial fan and the centrifugal separator, respectively, and wherein the fan drive motor and the separator drive motor have a common axle which is fixed with respect to a housing, and the fan drive motor includes a stator which is seated on a peripheral surface of the common axle, and the separator drive motor has a stator which is fastened to a radial outside of a carrying socket which is fastened to the common axle, and the fan drive motor includes a rotor with bearings and the separator drive motor includes a rotor with bearings and wherein the fan drive motor bearings and the separator drive motor bearings are carried by the common axle; and, wherein the control unit is arranged in a region between the fan drive motor and the separator drive motor.

20. A suction device for dental, medical and industrial purposes comprising:

a radial fan which exhibits a suction side and a pressure side;

a centrifugal separator, an air outlet of which is connected to the suction side of the radial fan;

at least one drive unit which includes an electric motor and serves for driving the radial fan and the centrifugal separator; and, a control unit for the drive unit, wherein the drive unit includes a fan drive motor and a separator drive motor, which are arranged in series, rotationally decoupled, and drive the radial fan and the centrifugal separator, respectively, and wherein the fan drive motor and the separator drive motor have a common axle which is fixed with respect to a housing, and the fan drive motor includes a stator which is seated on a peripheral surface of the common axle, and the separator drive motor has a stator which is fastened to a radial outside of a carrying socket which is fastened to the common axle, and the fan drive motor includes a rotor with bearings and the separator drive motor includes a rotor with bearings and wherein the fan drive motor bearings and the separator drive motor bearings are carried by the common axle; and, wherein the control unit includes two supply circuits which energise the fan drive motor and the separator drive motor at different rotational speeds.

21. A suction device for dental, medical and industrial purposes comprising:

a radial fan which exhibits a suction side and a pressure side;

a centrifugal separator, an air outlet of which is connected to the suction side of the radial fan;

at least one drive unit which includes an electric motor and serves for driving the radial fan and the centrifugal separator; and, a control unit for the drive unit, wherein the drive unit includes a fan drive motor and a separator drive motor, which are arranged in series, rotationally decoupled, and drive the radial fan and the centrifugal separator, respectively, and wherein the fan drive motor and the separator drive motor have a common axle which is fixed with respect to a housing, and the fan drive motor includes a stator which is seated on a peripheral surface of the common axle, and the separator drive motor has a stator which is fastened to a radial outside of a carrying socket which is fastened to the common axle, and the fan drive motor includes a rotor with bearings and the separator drive motor includes a rotor with bearings and wherein the fan drive motor bearings and the separator drive motor bearings are carried by the common axle; and, wherein at least one of the two drive motors has an axial dimension that is distinctly smaller than a radial dimension of the radial fan.

* * * * *

UNITED STATES PATENT AND TRADEMARK OFFICE
CERTIFICATE OF CORRECTION

PATENT NO. : 8,342,822 B2
APPLICATION NO. : 12/518536
DATED : January 1, 2013
INVENTOR(S) : Thoms et al.

Page 1 of 1

It is certified that error appears in the above-identified patent and that said Letters Patent is hereby corrected as shown below:

| | |
|---|---|
| Col. 15, line 23, Claim 5 | After "device of" delete "to". |
| Col. 15, line 35, Claim 7 | After "extending in" insert -- a longitudinal --. |
| Col. 15, line 60, Claim 13 | After "impeller" insert -- revolving --. |

Signed and Sealed this
Fifth Day of March, 2013

Teresa Stanek Rea
*Acting Director of the United States Patent and Trademark Office*